(12) United States Patent
Kiji

(10) Patent No.: US 11,932,623 B2
(45) Date of Patent: Mar. 19, 2024

(54) URACIL COMPOUNDS AND USE THEREOF

(71) Applicant: Sumitomo Chemical Company, Limited, Tokyo (JP)

(72) Inventor: Toshiyuki Kiji, Gifu (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 651 days.

(21) Appl. No.: 16/973,618

(22) PCT Filed: Jun. 10, 2019

(86) PCT No.: PCT/JP2019/022939
§ 371 (c)(1),
(2) Date: Dec. 9, 2020

(87) PCT Pub. No.: WO2019/240082
PCT Pub. Date: Dec. 19, 2019

(65) Prior Publication Data
US 2021/0163446 A1  Jun. 3, 2021

(30) Foreign Application Priority Data
Jun. 11, 2018 (JP) .................. 2018-110924

(51) Int. Cl.
C07D 401/12 (2006.01)
A01N 43/54 (2006.01)
A01P 13/00 (2006.01)

(52) U.S. Cl.
CPC .......... C07D 401/12 (2013.01); A01N 43/54 (2013.01); A01P 13/00 (2021.08)

(58) Field of Classification Search
CPC ...... C07D 401/12; A01N 43/54; A01N 13/00; A01N 13/02
See application file for complete search history.

(56) References Cited

U.S. PATENT DOCUMENTS

| | | | |
|---|---|---|---|
| 4,859,229 A | 8/1989 | Wenger et al. | |
| 6,537,948 B1 | 3/2003 | Tohyama et al. | |
| 2004/0254077 A1 | 12/2004 | Tohyama et al. | |

FOREIGN PATENT DOCUMENTS

| | | |
|---|---|---|
| AU | 6858991 A | 6/1992 |
| CN | 104661518 A | 5/2015 |
| EP | 0255047 A1 | 2/1988 |
| IL | 167955 B | 10/2007 |
| JP | S63041466 A | 2/1988 |
| JP | 2002155061 A | 5/2002 |
| RU | 2272035 C2 | 3/2006 |
| WO | 2003014109 A1 | 2/2003 |
| WO | 2006061562 A1 | 6/2006 |
| WO | 2014018400 A1 | 1/2014 |

OTHER PUBLICATIONS

Cotton. Advanced Inorganic Chemistry, 1999, inside cover (Year: 1999).*
Office Action dated Mar. 28, 2023 in BR Application No. 112020023928-3.
Office Action dated Jun. 21, 2022 in IN Application No. 202147000165.
English Translation of International Preliminary Report on Patentability dated Dec. 15, 2020 in International Application No. PCT/JP2019/022939.
English Translation of International Search Report dated Jul. 9, 2019 in International Application No. PCT/JP2019/022939.

* cited by examiner

*Primary Examiner* — Noble E Jarrell
(74) *Attorney, Agent, or Firm* — Panitch Schwarze Belisario & Nadel LLP

(57) ABSTRACT

A compound represented by the following formula (A) has excellent control efficacy against weeds, and shows high safety against useful plants.

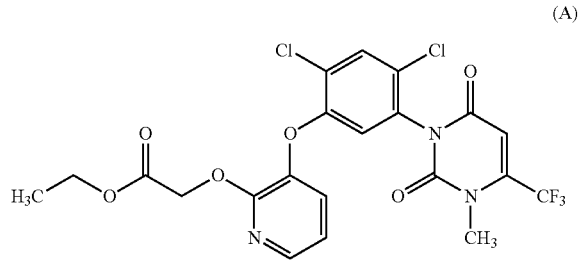

(A)

3 Claims, No Drawings

URACIL COMPOUNDS AND USE THEREOF

CROSS-REFERENCE TO RELATED APPLICATIONS

This application is a Section 371 of International Application No. PCT/JP2019/022939, filed Jun. 10, 2019, which was published in the Japanese language on Dec. 19, 2019 under International Publication No. WO 2019/240082 A1, which claims priority under 35 U.S.C. § 119(b) to Japanese Application No. 2018-110924, filed on Jun. 11, 2018, the disclosures of which are incorporated herein by reference in their entireties.

The present invention relates to a uracil compound and use thereof.

BACKGROUND ART

The patent document 1 describes that a compound represented by formula (B):

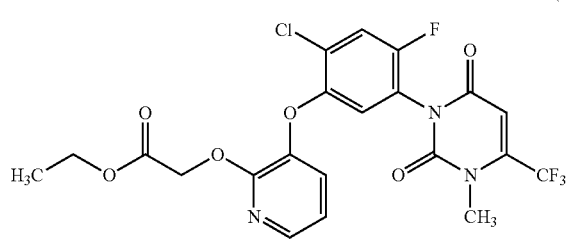

(B)

(hereinafter, referred to as Compound B) has an efficacy on controlling weeds.

CITATION LIST

Patent Document

Patent Document 1: U.S. Pat. No. 6,537,948 B2

SUMMARY OF THE INVENTION

Problems to be Solved by Invention

An object of the present invention is to provide a compound having excellent control efficacy on weeds, and showing high safety against useful plants.

Means to Solve Problems

The present inventor has intensively studied the above-mentioned problems, and found that a compound represented by the following formula (A) has some excellent efficacy on controlling weeds, and shows high safety against useful plants, which thus completed the present invention.

The present invention is as follows.

[1] A compound represented by formula (A):

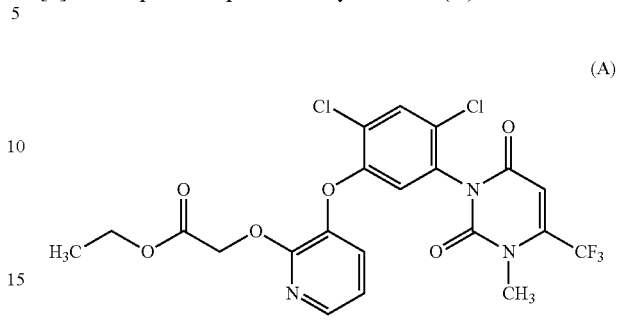

(A)

(hereinafter, referred to as "Compound A").

[2] A herbicidal composition comprising the compound according to [1] and an inert carrier (hereinafter, referred to as "Present composition A" or "Composition A of the present invention").

[3] A method for controlling weeds which comprises applying an effective amount of the compound according to [1] to weeds or a place where weeds are growing or will grow (hereinafter, referred to as "Present control method" or "Control method of the present invention").

Effect of Invention

The compound A has an excellent control efficacy on weeds, and shows high safety against useful plants, and is effective as an active ingredient for herbicidal composition.

MODE FOR CARRYING OUT THE INVENTION

The composition A of the present invention comprises the compound A and an inert carrier. The composition A of the present invention is usually prepared by mixing the compound A with an inert carrier such as solid carrier or liquid carrier, and if necessary, adding surfactants and the other auxiliary agents for formulation, to formulate into wettable powders, water dispersible granules, flowables, granules, dry flowables, emulsifiable concentrates, microcapsules and the others. These formulations comprises usually 0.1 to 99% by weight of the compound A.

Examples of the solid carrier to be used in the formulation include fine powders or granules of clays (for example, kaolin clay, diatomaceous earth, bentonite, or acid white clay), dry silica, wet silica, talcs, ceramics, other inorganic minerals (for example, sericite, quartz, sulfur, active carbon, or calcium carbonate) or chemical fertilizers (for example, ammonium sulfate, ammonium phosphate, ammonium nitrate, urea, or ammonium chloride) and the others; as well as synthetic resins (for example, polyester resins such as polypropylene, polyacrylonitrile, polymethyl methacrylate or polyethylene terephthalate; nylon resins (for example, nylon-6, nylon-11, or nylon-66); polyamide resins; polyvinyl chloride, polyvinylidene chloride, vinyl chloride-propylene copolymers, and the others).

Examples of the liquid carriers include water; alcohols (for example, methanol or ethanol); ketones (for example, acetone or methyl ethyl ketone); aromatic hydrocarbons (for example, toluene, xylene, ethyl benzene or methylnaphthalene); aliphatic hydrocarbons (for example, hexane, cyclohexane or kerosene); esters (for example, ethyl acetate or butyl acetate); nitriles (for example, acetonitrile or isobutyronitrile); ethers (for example, diisopropyl ether or diethyleneglycol dimethyl ether); amides (for example, N,N-dimethylformamide (hereinafter, referred to as DMF) or N,N-dimethylacetamide); sulfoxides (for example, dimethyl sulfoxide); propylene carbonate; and vegetable oils (for example, soybean oil or cottonseed oil).

Examples of the surfactants include nonionic surfactants such as polyoxyethylenated alkyl ethers, polyoxyethylenated alkyl aryl ethers, and polyethylene glycol fatty acid esters; and anionic surfactants such as alkyl sulfonates, alkylbenzene sulfonates and alkyl sulfates.

Examples of the other auxiliary agents for formulation include a binder, a dispersant, a colorant and a stabilizer, and specific examples thereof include casein, gelatin, polysaccharides (for example, starch, gum arabic, cellulose derivatives and alginic acid), lignin derivatives, bentonite, water-soluble synthetic polymers (for example, polyvinyl alcohol, polyvinyl pyrrolidone and polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

The method for controlling weeds of the present invention comprises applying an effective amount of the compound A to weeds or a place where weeds are growing or will grow. In the method for controlling weeds of the present invention, usually, the compound A is used in the form of the composition A. Examples of the method for controlling weeds of the present invention include a method of applying the composition A to stems and leaves of weeds, a method of applying the composition A to a surface of soil where weeds are growing or will grow, a method of incorporating the composition A into soil where weeds are growing, and a method of applying the composition A to a surface water of paddy field whose area where weeds are growing or will grow is flooded. In the method for controlling weeds of the present invention, the compound A is used usually 5 to 5,000 g per one (1) hectare of an area of a place where weeds are controlled.

The compound A may be used in an agricultural land and the like where useful plants as crops are grown to control weeds in the agricultural land.

Examples of the useful plants include the followings.

corn, rice, wheat, barley, rye, oat, sorghum, cotton, soybean, peanut, sugar beet, rapeseed, sunflower, sugar cane, tobacco, and hops, etc.;

Solanaceous vegetables (such as eggplant, tomato, bell pepper, pepper, and potato, etc.);

Cucurbitaceous vegetables (such as cucumber, pumpkin, zucchini, watermelon, melon, and squash, etc.);

Cruciferous vegetables (such as Japanese radish, turnip, horseradish, kohlrabi, Chinese cabbage, cabbage, leaf mustard, broccoli, and cauliflower, etc.);

Asteraceous vegetables (such as burdock, crown daisy, artichoke, and lettuce, etc.);

Liliaceous vegetables (such as green onion, onion, garlic, and asparagus, etc.);

Umbelliferous vegetables (such as parsley, celery, and parsnip, etc.);

Chenopodiaceous vegetables (such as spinach, and Swiss chard, etc.);

Lamiaceous vegetables (such as *Perilla frutescens*, mint, and basil, etc.);

Leguminous vegetables (such as green pea, kidney bean, adzuki bean, broad bean, and chickpea, etc.);

strawberry, sweet potato, *Dioscorea japonica, Colocasia,* Elephant roots, ginger, and okra, etc.;

Pomaceous fruits (such as apple, Japanese pear, common pear, Chinese quince, and quince);

Stone fleshy fruits (such as peach, plum, nectarine, Japanese plum, cherry, apricot, and prune, etc.);

Citrus plants (such as Satsuma mandarin, orange, lemon, lime, and grapefruit, etc.);

Nuts (such as chestnut, walnut, hazel nut, almond, pistachio, cashew nut, and macadamia nut, etc.);

Berry fruits (such as blueberry, cranberry, blackberry, and raspberry, etc.);

grape, persimmon, olive, loquat, banana, coffee, date, coconut palm, and oil palm, etc.

The useful plants described above include also genetically-engineered plants.

Examples of the weeds as a subject to be controlled by the compound A include the followings.

Urticaceae weeds: for example, *Urtica urens;*

Polygonaceae weeds: for example, *Polygonum convolvulus, Polygonum lapathifolium, Polygonum pensylvanicum, Polygonum persicaria, Polygonum longisetum, Polygonum aviculare, Polygonum arenastrum, Polygonum cuspidatum, Rumex japonicus, Rumex crispus, Rumex obtusifolius,* or *Rumex acetosa,* etc.;

Portulacaceae weeds: for example, *Portulaca oleracea,* etc.;

Caryophyllaceae weeds: for example, *Stellaria media, Stellaria aquatica, Cerastium holosteoides, Cerastium glomeratum, Spergula arvensis,* or *Silene gallica,* etc.;

Molluginaceae weeds: for example, *Mollugo verticillata,* etc.;

Chenopodiaceae weeds: for example, *Chenopodium album, Chenopodium ambrosioides, Kochia scoparia, Salsola kali,* or *Atriplex* spp., etc.;

Amaranthaceae weeds: for example, *Amaranthus retroflexus, Amaranthus viridis, Amaranthus lividus, Amaranthus spinosus, Amaranthus hybridus, Amaranthus palmeri, Amaranthus patulus, Amaranthus tuberculatus, Amaranthus blitoides, Amaranthus deflexus, Amaranthus quitensis, Alternanthera philoxeroides, Alternanthera sessilis,* or *Alternanthera tenella,* etc.;

Papaveraceae weeds: for example, *Papaver rhoeas, Papaver dubium,* or *Argemone mexicana,* etc.;

Brassicaceae weeds: for example, *Raphanus raphanistrum, Raphanus sativus, Sinapis arvensis, Capsella bursa-pastoris, Brassica juncea, Brassica napus, Descurainia pinnata, Rorippa islandica, Rorippa sylvestris, Thlaspi arvense, Myagrum rugosum, Lepidium virginicum,* or *Coronopus didymus,* etc.;

Capparaceae weeds: for example, *Cleome affinis,* etc.;

Fabaceae weeds: for example, *Aeschynomene indica, Aeschynomene rudis, Sesbania exaltata, Cassia obtusifolia, Cassia occidentalis, Desmodium tortuosum, Desmodium adscendens, Desmodium illinoense, Trifolium repens, Pueraria lobata, Vicia angustifolia, Indigofera hirsuta, Indigofera truxillensis,* or *Vigna sinensis,* etc.;

Oxalidaceae weeds: for example, *Oxalis corniculata, Oxalis strica,* or *Oxalis oxyptera,* etc.;

Geraniaceae weeds: for example, *Geranium carolinense,* or *Erodium cicutarium,* etc.;

Euphorbiaceae weeds: for example, *Euphorbia helioscopia, Euphorbia maculata, Euphorbia humistrata, Euphorbia esula, Euphorbia heterophylla, Euphorbia brasiliensis, Acalypha australis, Croton glandulosus, Croton lobatus, Phyllanthus corcovadensis,* or *Ricinus communis,* etc.;

Malvaceae weeds: for example, *Abutilon theophrasti, Sida rhombifolia, Sida cordifolia, Sida spinosa, Sida glazio-* vii, *Sida santaremnensis, Hibiscus trionum, Anoda cristata,* or *Malvastrum coromandelianum,* etc.;

Onagraceae weeds: for example, *Ludwigia epilobioides, Ludwigia octovalvis, Ludwigia decurre, Oenothera biennis,* or *Oenothera laciniata,* etc.;

Sterculiaceae weeds: for example, *Waltheria indica,* etc.;

Violaceae weeds: for example, *Viola arvensis,* or *Viola tricolor,* etc.;

Cucurbitaceae weeds: for example, *Sicyos angulates, Echinocystis lobata,* or *Momordica charantia,* etc.;

Lythraceae weeds: for example, *Ammannia multiflora, Ammannia auriculata, Ammannia coccinea, Lythrum salicaria,* or *Rotala indica,* etc.;

Elatinaceae weeds: for example, *Elatine triandra,* or *Elatine californica,* etc.;

Apiaceae weeds: for example, *Oenanthe javanica, Daucus carota,* or *Conium maculatum,* etc.;

Araliaceae weeds: for example, *Hydrocotyle sibthorpioides,* or *Hydrocotyle ranunculoides,* etc.;

Ceratophyllaceae weeds: for example, *Ceratophyllum demersum,* etc.;

Cabombaceae weeds: for example, *Cabomba caroliniana,* etc.;

Haloragaceae weeds: for example, *Myriophyllum aquaticum, Myriophyllum verticillatum, Myriophyllum spicatum,* or *Myriophyllum heterophyllum,* etc.;

Sapindaceae weeds: for example, *Cardiospermum halicacabum,* etc.;

Primulaceae weeds: for example, *Anagallis arvensis,* etc.;

Asclepiadaceae weeds: for example, *Asclepias syriaca,* or *Ampelamus albidus,* etc.;

Rubiaceae weeds: for example, *Galium aparine, Galium spurium* var. *echinospermon, Spermacoce latifolia, Richardia brasiliensis,* or *Borreria alata,* etc.;

Convolvulaceae weeds: for example, *Ipomoea nil, Ipomoea hederacea, Ipomoea purpurea, Ipomoea hederacea* var. *integriuscula, Ipomoea lacunosa, Ipomoea triloba, Ipomoea acuminata, Ipomoea hederifolia, Ipomoea coccinea, Ipomoea quamoclit, Ipomoea grandifolia, Ipomoea aristolochiafolia, Ipomoea cairica, Convolvulus arvensis, Calystegia hederacea, Calystegia japonica, Merremia hedeacea, Merremia aegyptia, Merremia cissoides,* or *Jacquemontia tamnifolia,* etc.;

Boraginaceae weeds: for example, *Myosotis arvensis,* etc.;

Lamiaceae weeds: for example, *Lamium purpureum, Lamium amplexicaule, Leonotis nepetaefolia, Hyptis suaveolens, Hyptis lophanta, Leonurus sibiricus,* or *Stachys arvensis,* etc.;

Solanaceae weeds: for example, *Datura stramonium, Solanum nigrum, Solanum americanum, Solanum ptycanthum, Solanum sarrachoides, Solanum rostratum, Solanum aculeatissimum, Solanum sisymbriifolium, Solanum carolinense, Physalis angulata, Physalis subglabrata,* or *Nicandra physaloides,* etc.;

Scrophulariaceae weeds: for example, *Veronica hederaefolia, Veronica persica, Veronica arvensis, Lindernia procumbens, Lindernia dubia, Lindernia angustifolia, Bacopa rotundifolia, Dopatrium junceum,* or *Gratiola japonica,* etc.;

Plantaginaceae weeds: for example, *Plantago asiatica, Plantago lanceolata, Plantago major,* or *Callitriche palustris,* etc.;

Asteraceae weeds: for example, *Xanthium pensylvanicum, Xanthium occidentale, Xanthium italicum, Helianthus annuus, Matricaria chamomilla, Matricaria perforata, Chrysanthemum segetum, Matricaria matricarioides, Artemisia princeps, Artemisia vulgaris, Artemisia verlotorum, Solidago altissima, Taraxacum officinale, Galinsoga ciliata, Galinsoga parviflora, Senecio vulgaris, Senecio brasiliensis, Senecio grisebachii, Conyza bonariensis, Conyza smatrensis, Conyza canadensis, Ambrosia artemisiaefolia, Ambrosia trifida, Bidens tripartita, Bidens pilosa, Bidens frondosa, Bidens subalternans, Cirsium arvense, Cirsium vulgare, Silybum marianum, Carduus nutans, Lactuca serriola, Sonchus oleraceus, Sonchus asper, Wedelia glauca, Melampodium perfoliatum, Emilia sonchifolia, Tagetes minuta, Blainvillea latifolia, Tridax procumbens, Porophyllum ruderale, Acanthospermum australe, Acanthospermum hispidum, Cardiospermum halicacabum, Ageratum conyzoides, Eupatorium perfoliatum, Eclipta alba, Erechtites hieracifolia, Gamochaeta spicata, Gnaphalium spicatum, Jaegeria hirta, Parthenium hysterophores, Siegesbeckia orientails, Soliva sessilis, Eclipta prostrata, Eclipta alba,* or *Centipeda minima,* etc.;

Alismataceae weeds: for example, *Sagittaria pygmaea, Sagittaria trifolia, Sagittaria sagittifolia, Sagittaria montevidensis, Sagittaria aginashi, Alisma canaliculatum,* or *Alisma plantago-aquatica,* etc.;

Limnocharitaceae weeds: for example, *Limnocharis flava,* etc.;

Hydrocharitaceae weeds: for example, *Limnobium spongia, Hydrilla verticillata,* or *Najas guadalupensis,* etc.;

Araceae weeds: for example, *Pistia stratiotes,* etc.;

Lemnaceae weeds: for example, *Lemna aoukikusa, Spirodela polyrhiza,* or *Wolffia* spp, etc.;

Potamogetonaceae weeds: for example, *Potamogeton distinctus, Potamogeton crispus, Potamogeton illinoensis,* or *Stuckenia pectinata,* etc.;

Liliaceae weeds: for example, *Allium canadense, Allium vineale,* or *Allium macrostemon,* etc.;

Pontederiaceae weeds: for example, *Eichhornia crassipes, Heteranthera limosa, Monochoria korsakowii,* or *Monochoria vaginalis,* etc.;

Commelinaceae weeds: for example, *Commelina communis, Commelina bengharensis, Commelina erecta,* or *Murdannia keisak,* etc.;

Poaceae weeds: for example, *Echinochloa crus-galli, Echinochloa oryzicola, Echinochloa crus-galli* var *formosensis, Echinochloa oryzoides, Echinochloa colona, Echinochloa crus-pavonis, Setaria viridis, Setaria faberi, Setaria glauca, Setaria geniculata, Digitaria ciliaris, Digitaria sanguinalis, Digitaria horizontalis, Digitaria insularis, Eleusine indica, Poa annua, Poa trivialis, Poa pratensis, Alospecurus aequalis, Alopecurus myosuroides, Avena fatua, Sorghum halepense, Sorghum vulgare, Agropyron repens, Lolium multiflorum, Lolium perenne, Lolium rigidum, Bromus catharticus, Bromus sterilis, Bromus japonicus, Bromus secalinus, Bromus tectorum, Hordeum jubatum, Aegilops cylindrica, Phalaris arundinacea, Phalaris minor, Apera spica-venti, Panicum dichotomiflorum, Panicum texanum, Panicum maximum, Brachiaria platyphylla, Brachiaria ruziziensis, Brachiaria plantaginea, Brachiaria decumbens, Brachiaria brizantha, Brachiaria humidicola, Cenchrus echinatus, Cenchrus pauciflorus, Eriochloa villosa, Pennisetum setosum, Chloris gayana, Chlorisvirgata, Eragrostis pilosa, Rhynchelitrum repens, Dactyloctenium aegyptium, Ischaemum rugosum, Isachne globosa, Oryza sativa, Paspalum notatum, Paspalum maritimum, Paspalum distichum, Pennisetum clandestinum, Pennisetum setosum, Rottboellia cochinchinensis, Leptochloa chinensis, Leptochloa fascicularis, Leptochloa filiformis, Leptochloa panicoides, Leersia japonica, Leersia sayanuka, Leersia oryzoides, Glyceria leptorrhiza, Glyceria acutiflora, Glyceria* maxima, Agrostis gigantea, Agrostis stolonifera, Cynodon dactylon, Dactylis glomerata, Eremochloa ophiuroides, Festuca arundinacea, Festuca rubra, Imperata cylindrica, Miscanthus sinensis, Panicum virgatum, or Zoysia japonica, etc.;

Cyperaceae weeds: for example, Cyperus microiria, Cyperus iria, Cyperus compressus, Cyperus difformis, Cyperus flaccidus, Cyperus globosus, Cyperus nipponicus, Cyperus odoratus, Cyperus serotinus, Cyperus rotundus, Cyperus esculentus, Kyllinga gracillima, Kyllinga brevifolia, Fimbristylis miliacea, Fimbristylis dichotoma, Eleocharis acicularis, Eleocharis kuroguwai, Schoenoplectiella hotarui, Schoenoplectiella juncoides, Schoenoplectiella wallichii, Schoenoplectiella mucronatus, Schoenoplectiella triangulatus, Schoenoplectiella nipponicus, Schoenoplectiella triqueter, Bolboschoenus koshevnikovii, or Bolboschoenus fluviatilis, etc.;

Equisetaceae weeds: for example, Equisetum arvense, or Equisetum palustre, etc.;

Salviniaceae weeds: for example, Salvinia natans, etc.;

Azollaceae weeds: for example, Azolla japonica, or Azolia imbricata, etc.;

Marsileaceae weeds: for example, Marsilea quadrifolia, etc.;

Others: filamentous algae (for example, Pithophora, Cladophora), mosess, liverwort, hornwort, cyanobacteria, bracken, and sucker of permanent crops (for example, pome fruits, stone fruits, berry fruits, nut fruit, citrus fruit, hop, or grapes etc.).

EXAMPLES

Hereinafter, the present invention is explained in more detail by using Preparation Example, Formulation Example, and Test Example and the like, however, the present invention should not be limited to these examples.

The Preparation Examples of the compound A are shown.

Step 1

To a mixture of 2,4-dichloro-5-aminophenol 50 g and t-butyl methyl ether 500 mL was added dropwise N,N-diethylaniline 49.7 mL at 0° C., followed by adding dropwise of a mixture of ethyl chloroformate 26.9 mL and t-butyl methyl ether 50 mL at 0° C. The resulting mixture was stirred under reflux for 3 hours. The resulting mixture was added to ice water 1 L, and the mixture was extracted with ethyl acetate. The resulting organic layers were washed with 1N hydrochloric acid and brine successively, dried over anhydrous sodium sulfate, and concentrated under reduced pressure. The resulting residue was washed with 10% ethyl acetate/hexane to obtain an intermediate compound A represented by the following formula 47.0 g.

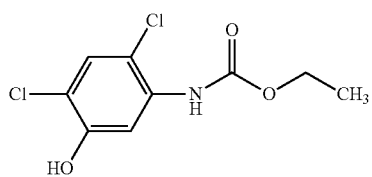

Intermediate Compound A: $^1$H-NMR (DMSO-$d_6$) δ (ppm): 1.23 (3H, t), 4.12 (2H, q), 7.33 (1H, s), 7.46 (1H, s), 8.90, (1H, s), 10.52 (1H, s).

Step 2

To a mixture of sodium hydride (60%, in oil) 10.1 g and N,N-dimethylformamide hereinafter, referred to as DMF) 180 mL was added portionwise the intermediate compound A 30.0 g under nitrogen atmosphere at 0° C. To the resulting mixture was added dropwise a mixture of ethyl 3-amino-4,4,4-trifluorocrotonate 19.4 mL and DMF 120 mL at 0° C. The resulting mixture was stirred at 100° C. for 5 hours. The resulting mixture was added to ice water, and the mixture was extracted with ethyl acetate. The resulting organic layers were washed with water and brine successively, dried over anhydrous sodium sulfate, and concentrated under reduced pressure. The resulting residue was washed with 10% ethyl acetate/hexane to obtain an intermediate compound B represented by the following formula 27.0 g.

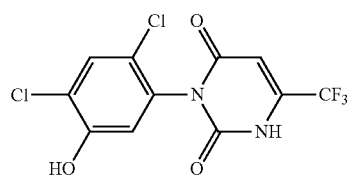 [SMILES: O=c1cc(C(F)(F)F)[nH]c(=O)n1-c1cc(O)c(Cl)cc1Cl]

Intermediate compound B: $^1$H-NMR (DMSO-$d_6$) δ (ppm): 6.41 (1H, s), 7.10 (1H, s), 7.69 (1H, s), 10.85 (1H, s), 12.70 (1H, br s).

Step 3

To a mixture of the intermediate compound B 25.0 g and acetone 250 mL were added potassium carbonate 30.2 g and methyl iodide 18.3 ml successively, and the mixture was stirred under reflux for 3 hours. To the resulting mixture was added water, and the mixture was extracted with ethyl acetate. The resulting organic layers were washed with brine, dried over anhydrous sodium sulfate, and concentrated under reduced pressure. The resulting residue was washed with 5% ethyl acetate/hexane to obtain an intermediate compound C represented by the following formula 18.0 g.

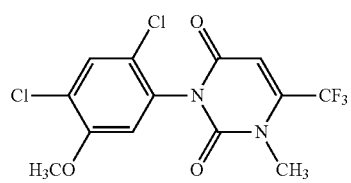 [SMILES: COc1cc(-n2c(=O)cc(C(F)(F)F)n(C)c2=O)c(Cl)cc1Cl]

Intermediate Compound C: $^1$H-NMR (DMSO-$d_6$) δ (ppm): 3.44 (3H, s), 3.83 (3H, s), 6.63 (1H, s), 7.40 (1H, s), 7.83 (1H, s).

Step 4

To a mixture of the intermediate compound C 18.0 g and dichloromethane 180 mL was added boron tribromide 9.40 mL at 0° C., and the mixture was stirred at room temperature for 1 hour. The resulting mixture was added to ice water, and the mixture was extracted with dichloromethane. The resulting organic layers were washed with saturated sodium bicarbonate water and brine, dried over anhydrous sodium sulfate, and concentrated under reduced pressure. The resulting residue was washed with 5% ethyl acetate/hexane to obtain an intermediate compound D represented by the following formula 14.0 g.

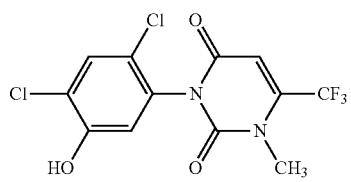

Intermediate Compound D: $^1$H-NMR (DMSO-$d_6$) δ (ppm): 3.41 (3H, s), 6.58 (1H, s), 7.07 (1H, s), 7.70 (1H, s), 10.88 (1H, s).

Step 5

To a mixture of the intermediate compound D 14.0 g and acetone 112 mL was added potassium carbonate 10.9 g. To the resulting mixture were added 2-chloro-3-oxobutanamide 8.02 g and acetone 28 mL, and the mixture was stirred under reflux for 12 hours. The resulting mixture was concentrated under reduced pressure, and the residue was dissolved into water. The resulting mixture was extracted with ethyl acetate, and the resulting organic layers were washed with brine, dried over anhydrous sodium sulfate, and concentrated under reduced pressure. The resulting residue was subjected to a silica gel column chromatography (30% ethyl acetate/hexane) to obtain an intermediate compound E represented by the following formula 8.00 g.

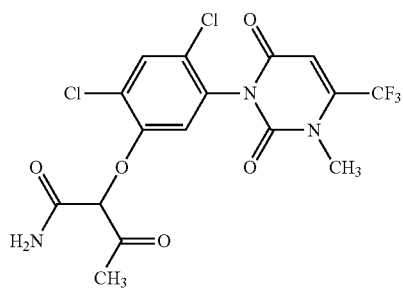 [SMILES: CC(=O)C(Oc1cc(-n2c(=O)cc(C(F)(F)F)n(C)c2=O)c(Cl)cc1Cl)C(N)=O]

Intermediate Compound E: $^1$H-NMR (DMSO-$d_6$) δ (ppm): 1.71 (1.2H, s), 2.30 (1.8H, s), 3.41 (1.2H, s), 3.43 (1.8H, s), 5.24 (0.6H, s), 6.55 (0.4H, s), 6.62 (0.6H, s), 7.15 (0.6H, s), 7.21 (0.4H, s), 7.62 (0.8H, br s), 7.72 (0.6H, br s), 7.76 (0.6H, br s), 7.88 (0.4H, s), 7.92 (0.6H, s), 13.86 (0.4H, br s).

Step 6

To a mixture of the intermediate compound E 8.0 g, 1,1,3,3-tetramethoxypropane 3.78 mL and acetic acid 24 mL was added dropwise a solution of 33% hydrogen bromide/acetic acid 9.49 mL at 0° C. The resulting mixture was stirred at 50° C. for 4 hours, and then concentrated under reduced pressure. To the resulting mixture were added methanol 8 ml and water 72 mL, and the mixture was stirred at 50° C. for 1 hour. The resulting mixture was added slowly to cool saturated sodium bicarbonate water, and the mixture was extracted with ethyl acetate. The resulting organic layers were washed with brine, dried over anhydrous sodium sulfate, and concentrated under reduced pressure. The resulting residue was purified by a silica gel column chromatography (30% ethyl acetate/hexane) to obtain an intermediate compound F represented by the following formula 4.5 g.

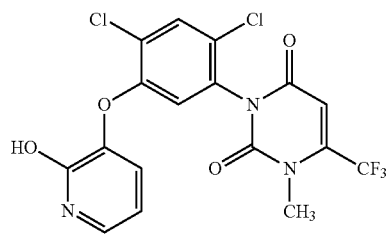 [SMILES: Cn1c(C(F)(F)F)cc(=O)n(-c2cc(Oc3cccnc3O)c(Cl)cc2Cl)c1=O]

Intermediate Compound F: $^1$H-NMR (DMSO-$d_6$) δ (ppm): 3.38 (3H, s), 6.22 (1H, t), 6.53 (1H, s), 7.03 (1H, s), 7.33-7.35 (1H, m), 7.41 (1H, d), 7.93 (1H, s), 12.11 (1H, s).

Step 7

To a mixture of the intermediate compound F 4.5 g and xylene 45 mL was added boron trifluoride diethyl ether complex 0.063 mL, followed by adding dropwise of ethyl diazoacetate 1.48 mL at 0° C. The resulting mixture was stirred at 40° C. for 4 hours, and thereto was then added an aqueous 15% sulfuric acid solution 18 mL, and the mixture was stirred at 40° C. for 1 hour. The resulting mixture was neutralized with an aqueous 27% sodium hydroxide solution, and the precipitated solids were filtered. The filtrates were concentrated under reduced pressure. The resulting residue was purified by a silica gel column chromatography (10% ethyl acetate/hexane) to obtain a compound A 3.1 g.

$^1$H-NMR data of the compound A is indicated below.

$^1$H-NMR (DMSO-$d_6$) δ (ppm): 1.15 (3H, t), 3.38 (3H, s), 4.10 (2H, q), 4.88 (2H, s), 6.56 (1H, s), 7.09 (1H, s), 7.13 (1H, dd), 7.59 (1H, d), 8.00-8.03 (2H, m).

Next, Formulation Examples of the compound A are described. Herein, the term "part(s)" means "part(s) by weight".

Formulation Example 1

Five (5) parts of the compound A, 2 parts of GERONOL (registered trademark) FF/4-E, 8 parts of GERONOL (registered trademark) FF/6-E, and 85 parts of SOLVESSO (registered trademark) 200 were mixed thoroughly to obtain a formulation.

Formulation Example 2

To 1.5 parts of the compound A, 2 parts of sodium lignin sulfonate, 40 parts of talc, and 56.5 parts of bentonite are added, followed by mixing. Then an appropriate amount of water is added to the mixture, and the resulting mixture is further stirred, and is granulated with a granulator, and is forced-air dried to obtain a formulation.

Formulation Example 3

Thirty-five (35) parts of a mixture of polyoxyethylene alkyl ether sulfate ammonium salt and wet silica (weight ratio of 1:1), 10 parts of the compound A, and 55 parts of water are mixed thoroughly to obtain a formulation.

Further, Test Examples are used to show an efficacy of the compound A on controlling weeds and safety against useful plants (phytotoxicity)

In the Test Examples as described below, for the assessment of weeds-controlling efficacy, the efficacy is defined as "0" if the condition of budding or growth of test pants in the treated area indicates little or no difference compared to that of the untreated area at the time of the investigation. The efficacy is defined as "100" if test weeds in the treated area are all dead or the budding or growth of test weeds is completely prevented. Hence, the efficacy is classified as "0 to 100".

The "untreated group" represents a group where a similar treatment procedure to that of the treated group except not using the compound A is done.

Test Example 1

A plastic pot was filled with soil. Ivyleaf morning glory (*Ipomoea hederacea*), Redroot pigweed (*Amaranthus retroflexus*) and corn were seeded to the plastic pot, and the plants are grown in a greenhouse for 15 days. A prescribed amount of the formulation prepared by the method of the formulation example 1 was diluted with water containing 1% of Agridex (registered trademark) to obtain a diluted solution. The diluted solution was uniformly sprayed at a rate of 204 L/ha from the upper side of the plants such that the applied dose of the compound A was made to 20 gai/ha or 10 gai/ha. Thereafter, the plants were grown in a greenhouse for 11 days, and the control efficacies were assessed by the above-mentioned method. The results are shown in [Table 1].

TABLE 1

| Applied dose [gai/ha] | Amaranthus retroflexus | Ipomoea hederacea | Corn |
| --- | --- | --- | --- |
| 20 | 100 | 100 | 20 |
| 10 | 100 | 100 | 5 |

The compound A showed high efficacies on controlling weeds against Redroot pigweed (*Amaranthus retroflexus*) and Ivyleaf morning glory (*Ipomoea hederacea*). Further, the compound A showed low phytotoxicity against corn, which thus suggested high safety against useful plants.

Comparative Test Example 1

The comparative test was conducted by using the compound B in place of the compound A according to a similar method to that described in the Test example 1. The test results are indicated in Table 2.

TABLE 2

| Applied dose [gai/ha] | Amaranthus retroflexus | Ipomoea hederacea | Corn |
| --- | --- | --- | --- |
| 20 | 100 | 100 | 100 |
| 10 | 100 | 100 | 100 |

The compound B showed high efficacies on controlling weeds against Redroot pigweed (*Amaranthus retroflexus*) and Ivyleaf morning glory (*Ipomoea hederacea*), and also high phytotoxicity against corn which is a useful plant.

INDUSTRIAL APPLICABILITY

The compound A has an excellent control efficacy against weeds, and shows high safety against useful plants, which is effective as an active ingredient for herbicidal composition.

The invention claimed is:
1. A compound represented by formula (A):

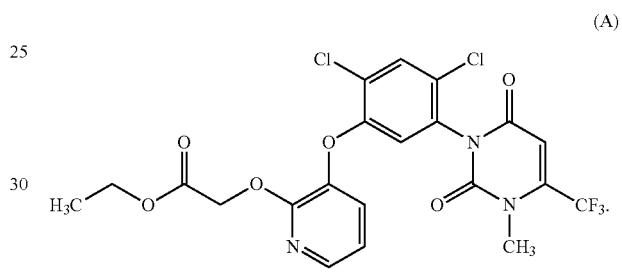

(A)

2. A herbicidal composition comprising the compound according to claim 1 and an inert carrier.
3. A method for controlling weeds which comprises applying an effective amount of the compound according to claim 1 to weeds or a place where weeds are growing or will grow.

* * * * *